(12) United States Patent
Talmer et al.

(10) Patent No.: US 9,523,699 B2
(45) Date of Patent: *Dec. 20, 2016

(54) APPARATUS AND METHODS FOR DISPENSING SAMPLE HOLDERS

(71) Applicant: Biokit, S.A., Barcelona (ES)

(72) Inventors: Mark Talmer, Pepperell, MA (US); Paul C. Dahlstrom, Hollis, NH (US)

(73) Assignee: Biokit, S.A. (ES)

( * ) Notice: Subject to any disclaimer, the term of this patent is extended or adjusted under 35 U.S.C. 154(b) by 550 days.

This patent is subject to a terminal disclaimer.

(21) Appl. No.: 13/923,505

(22) Filed: Jun. 21, 2013

(65) Prior Publication Data

US 2013/0280024 A1 Oct. 24, 2013

Related U.S. Application Data

(60) Division of application No. 12/756,608, filed on Apr. 8, 2010, now Pat. No. 8,480,954, which is a
(Continued)

(51) Int. Cl.
*G01N 35/00* (2006.01)
*B01L 9/06* (2006.01)
(Continued)

(52) U.S. Cl.
CPC ........... *G01N 35/00029* (2013.01); *B01L 9/06* (2013.01); *G01N 35/04* (2013.01);
(Continued)

(58) Field of Classification Search
CPC .... G01N 35/0092; G01N 21/00; G01N 35/04; G01N 35/00029
See application file for complete search history.

(56) References Cited

U.S. PATENT DOCUMENTS

| 1,643,883 A | 9/1927 | Fife |
| 3,653,540 A | 4/1972 | Offutt |
| (Continued) | | |

FOREIGN PATENT DOCUMENTS

| CA | 1063831 | 10/1979 |
| EP | 0712000 | 9/1995 |
| (Continued) | | |

OTHER PUBLICATIONS

International Search Report for International Application No. PCT/US02/33941 mailed Apr. 25, 2003.
(Continued)

*Primary Examiner* — Jonathan Hurst
(74) *Attorney, Agent, or Firm* — Burns & Levinson LLP

(57) ABSTRACT

An apparatus and methods for dispensing sample holders for use in an automated sample analyzer is disclosed herein. The apparatus for dispensing sample holders includes a rotating carousel for housing stack of sample holders. Stacks of sample holders from the rotating carousel are fed into a chute where sample holders contact a set of rotating members having helical threads thereon. The helically threaded rotating members engage the sample containers and separate each sample holder from the remaining sample holders in the stack by rotation of the helically threaded rotating members. The sample holder can then be transferred for use in an automated sample analyzer.

16 Claims, 12 Drawing Sheets

Related U.S. Application Data continuation of application No. 11/704,080, filed on Feb. 8, 2007, now Pat. No. 7,731,899.

(51) Int. Cl.
  *G01N 21/00* (2006.01)
  *G01N 35/04* (2006.01)

(52) U.S. Cl.
  CPC ........ *B01L 2200/141* (2013.01); *G01N 21/00* (2013.01); *G01N 35/0092* (2013.01); *G01N 2035/0465* (2013.01)

(56) References Cited

U.S. PATENT DOCUMENTS

| | | | |
|---|---|---|---|
| 3,703,336 A | 11/1972 | Rosse et al. | |
| 3,713,985 A | 1/1973 | Astle | |
| 3,775,595 A | 11/1973 | Rosse et al. | |
| 3,971,106 A | 7/1976 | Chambers | |
| 3,973,915 A | 8/1976 | Raffaele et al. | |
| 4,022,579 A | 5/1977 | Revillet et al. | |
| 4,120,662 A | 10/1978 | Fosslien | |
| 4,178,345 A | 12/1979 | Terk | |
| D257,175 S | 9/1980 | Terk | |
| D257,394 S | 10/1980 | Reichler | |
| 4,226,531 A | 10/1980 | Tiffany et al. | |
| D260,428 S | 8/1981 | Fekete | |
| 4,311,484 A * | 1/1982 | Fosslien | 73/864.21 |
| 4,313,735 A | 2/1982 | Yamashita et al. | |
| D265,124 S | 6/1982 | Terk | |
| 4,341,736 A | 7/1982 | Drbal et al. | |
| D266,589 S | 10/1982 | Gilford et al. | |
| 4,432,643 A | 2/1984 | Koisumi et al. | |
| D280,131 S | 8/1985 | Takasugi | |
| D282,005 S | 12/1985 | Kayhko | |
| 4,561,534 A * | 12/1985 | Nalbach | 198/400 |
| 4,582,684 A | 4/1986 | Vogel et al. | |
| 4,777,141 A | 10/1988 | Calzi et al. | |
| 4,778,763 A | 10/1988 | Makiguchi | |
| 4,787,744 A | 11/1988 | Hissung | |
| 4,877,659 A | 10/1989 | Vince | |
| 4,895,706 A | 1/1990 | Root et al. | |
| 4,929,426 A | 5/1990 | Bodai et al. | |
| 4,933,147 A | 6/1990 | Hollar et al. | |
| 5,084,246 A | 1/1992 | Lyman et al. | |
| 5,092,672 A | 3/1992 | Vanderwerf | |
| 5,098,663 A | 3/1992 | Berthold et al. | |
| D327,743 S | 7/1992 | Frenkel et al. | |
| 5,164,318 A | 11/1992 | Sato et al. | |
| D335,348 S | 5/1993 | Frenkel et al. | |
| 5,233,506 A | 8/1993 | Semenik et al. | |
| 5,266,268 A | 11/1993 | Antocci et al. | |
| 5,285,907 A | 2/1994 | Franchere et al. | |
| 5,333,717 A | 8/1994 | Rosenberg et al. | |
| 5,358,691 A | 10/1994 | Clark et al. | |
| 5,360,597 A | 11/1994 | Jakubowicz et al. | |
| 5,376,313 A | 12/1994 | Kanewski, III et al. | |
| 5,441,891 A | 8/1995 | Burkovich et al. | |
| 5,456,883 A | 10/1995 | Burkovich et al. | |
| 5,470,536 A | 11/1995 | Jarvimaki | |
| 5,518,693 A | 5/1996 | Tomasso et al. | |
| 5,522,255 A | 6/1996 | Neel et al. | |
| 5,536,664 A | 7/1996 | Switalski et al. | |
| 5,540,890 A | 7/1996 | Clark et al. | |
| 5,567,387 A | 10/1996 | Versluys et al. | |
| 5,567,617 A | 10/1996 | Caprio et al. | |
| 5,575,046 A | 11/1996 | Rourke | |
| 5,578,268 A | 11/1996 | Champseix et al. | |
| 5,599,501 A | 2/1997 | Carey et al. | |
| D382,347 S | 8/1997 | Grubb | |
| 5,665,558 A | 9/1997 | Frame et al. | |
| 5,735,387 A | 4/1998 | Polaniec et al. | |
| 5,795,784 A | 8/1998 | Arnquist et al. | |
| 5,888,835 A | 3/1999 | Bushnell et al. | |
| 5,902,548 A | 5/1999 | Watts et al. | |
| D413,391 S | 8/1999 | Lapeus et al. | |
| D413,677 S | 9/1999 | Dumitrescu et al. | |
| 5,948,363 A | 9/1999 | Gaillard | |
| D416,330 S | 11/1999 | Brown | |
| 5,985,671 A | 11/1999 | Leistner et al. | |
| 6,149,872 A | 11/2000 | Mack et al. | |
| 6,413,420 B1 | 7/2002 | Foy et al. | |
| 6,562,239 B2 | 5/2003 | Foy et al. | |
| D481,133 S | 10/2003 | Blouin et al. | |
| 7,731,899 B2 | 6/2010 | Talmer et al. | |
| 2003/0175156 A1 | 9/2003 | Ford | |
| 2003/0194799 A1 | 10/2003 | Achter et al. | |
| 2005/0207937 A1 | 9/2005 | Itoh | |
| 2005/0271550 A1 | 12/2005 | Talmer et al. | |
| 2006/0013729 A1 | 1/2006 | Carey et al. | |
| 2006/0110293 A1 | 5/2006 | Fichera | |

FOREIGN PATENT DOCUMENTS

| | | |
|---|---|---|
| EP | 0806665 | 5/1997 |
| EP | 0889328 | 1/1999 |
| EP | 0902548 A2 | 3/1999 |
| EP | 0965385 A2 | 12/1999 |
| FR | 627277 | 9/1927 |
| JP | 58-75516 | 5/1983 |
| JP | 1028561 | 1/1989 |
| JP | 04/248980 | 9/1992 |
| JP | 8146001 | 6/1996 |
| JP | 09187434 | 4/1998 |
| JP | 10123136 | 5/1998 |
| JP | 09340584 | 6/1999 |
| JP | 2000111557 | 4/2000 |
| JP | 2001116752 | 4/2001 |
| WO | 96/11866 | 4/1996 |
| WO | WO98/18008 | 4/1998 |
| WO | WO03/086637 | 10/2003 |
| WO | WO2005/124365 | 12/2005 |

OTHER PUBLICATIONS

International Search Report and Written Opinion of the International Searching Authority for International Application No. PCT/US08/52894, mailed Aug. 7, 2008 (7 pgs.).

Siemens Global website @ http://diagnostics.siemens.com/webapp/wcs/stores/servlet/Product, for ACS:180® SE Automated Chemiluminescence System accessed Jun. 13, 2007, © Siemens AG, 2007.

Supplementary European Search Report issued in a counterpart European patent application No. EP 08 72 8906 on Sep. 2, 2015 (8 pages).

* cited by examiner

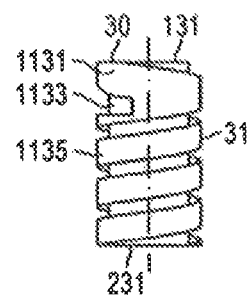
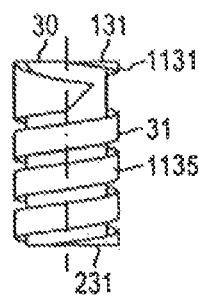
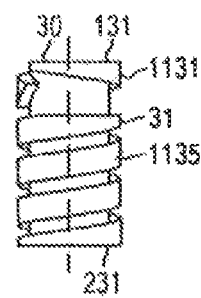
FIG. 6A  FIG. 6B  FIG. 6C
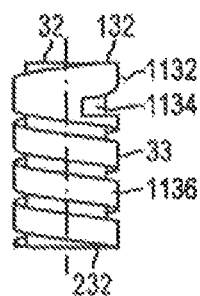
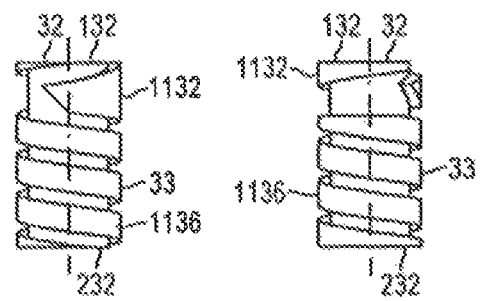
FIG. 7A  FIG. 7B  FIG. 7C

APPARATUS AND METHODS FOR DISPENSING SAMPLE HOLDERS

CROSS REFERENCE TO RELATED APPLICATION

This application is a divisional of application U.S. Ser. No. 12/756,608, filed on Apr. 8, 2010, now granted U.S. Pat. No. 8,480,954 which is a continuation application and claims priority to and the benefit of U.S. Ser. No. 11/704,080, filed on Feb. 8, 2007, now granted U.S. Pat. No. 7,731,899, the entire contents of which are incorporated herein by reference.

FIELD OF THE INVENTION

The invention relates to devices and methods for storing and dispensing cuvettes for use in an automated clinical sample analyzer.

BACKGROUND OF THE INVENTION

Automatic clinical sample analyzers are common in hospitals and research institutions for analyzing large quantities of samples. For example, environmental specimens, such as water, or patient specimens, such as blood, urine or other biological samples, can be tested using automated sample analyzers to determine concentrations of contaminants or analytes, for example.

Automated sample analyzers have a variety of component systems that work in concert to manipulate patient samples. For example, an automated sample analyzer may have one or more reagent dispensing components, sample holder dispensing components, sample and reagent probes, washing stations, detecting mechanisms, and automated arms, carousels, or conveyors for moving samples from one station to another.

Automated sample analyzers reduce time taken to perform assays on the samples, improve output, and reduce human error and contamination, thereby providing cost effective sample analysis. However, despite the automated functioning of such analyzers, operator intervention is often required if a component malfunctions, or if consumables, such as reagents and sample holders, need replacing. Therefore, there is a need in the art for an automated sample analyzer that reduces the need for operator intervention, thereby further improving efficiency, accuracy of testing, and throughput.

SUMMARY OF THE INVENTION

The invention is related to an apparatus and methods for dispensing sample holders for use in an automated clinical sample analyzer. In one aspect, the invention is directed to a device for separating a sample holder from a stack of sample holders. The device includes a support member for receiving a stack of at least two sample holders and at least one releasing member, preferably two releasing members. The support member is positioned to introduce at least one of the sample holders in the stack of sample holders between a first releasing member and a second releasing member. The first and second releasing members each include a helical thread. The first releasing member is operatively connected to a first rotator capable of rotation in a clockwise direction. The second releasing member is operatively connected to a second rotator capable of rotation in a counter-clockwise direction. The first and second rotators rotate the first and second releasing member thereby releasing one of the at least two sample holders from the stack of sample holders. In a further embodiment, the first rotator is further capable of rotation in a counter-clockwise direction while the second rotator is further capable of rotation in a clockwise direction. The rotator may comprise an oscillating motor in one embodiment.

According to the invention, in one embodiment, the releasing members are threaded. For example, in one embodiment, the first releasing member has a right hand oriented helical thread and the second releasing member has a left hand oriented helical thread. In one embodiment, the pitch of the right-hand helical thread is the same as the pitch of the left hand helical thread. Alternatively, the pitch of one helical thread differs from the pitch of another helical thread. The pitch is in the range of about 6.9°-7.3° in one embodiment, while in another embodiment, the pitch is in the range of about 9.2°-9.6°. In a further embodiment, the pitch is about 9.4°, while in another embodiment, the pitch is about 7.1°.

In yet another embodiment, the first releasing member has a right hand oriented helical thread and a left hand oriented helical thread. The second releasing member also has a right hand oriented helical thread and a left hand oriented helical thread. According to one embodiment, the pitch of the right hand helical thread of the first releasing member differs from the pitch of the left hand helical thread of the first releasing member. For example, the pitch of the right hand helical thread is in the range of about 6.9°-7.3° while the pitch of the left hand helical thread is in the range of about 9.2%9.6°. In a further embodiment, the pitch of the right hand helical thread is about 7.1° while the pitch of the left hand helical thread is about 9.4°.

In a further embodiment, the first releasing member is substantially cylindrical and has the same diameter as the second releasing member. In another embodiment, the diameter of the first releasing member is different than the diameter of the second releasing member. In yet another embodiment, the releasing member is tapered with the widest portion at the top, or alternatively, the widest portion is at the bottom.

The device according to the invention also includes a sample holder receiver, according to one embodiment of the invention. For example, the sample holder receiver receives the sample holder following separation of the first sample holder from the second sample holder.

In another embodiment, the support member for receiving a stack of at least two sample holders is a tube, while in another embodiment, the support member comprises at least two walls, each wall having a C-shaped cross-section.

The device, according to one embodiment, further comprises a rotating module, for example, a wheel, disc, or cylinder, having a plurality of openings for supporting stacks of sample holders. In one embodiment, each of the plurality of openings is positioned equidistant from the center of the carousel and equidistant from each other. In yet another embodiment, the plurality of openings are positioned around the circumference of the rotating carousel.

According to another aspect, the invention includes a method for separating a sample holder from a stack of sample holders. The method includes positioning a stack of at least two sample holders adjacent a first releasing member comprising a helical thread, rotating the first releasing member in a first direction, engaging said sample holder; disengaging the first sample holder from the stack of sample holders; rotating the first releasing member in a second direction; and releasing the sample holder from the stack of sample holders.

In a further embodiment, the method includes positioning the stack of sample holders adjacent a second releasing member. The releasing member, for example, includes a helical thread, in one embodiment, the first releasing member has a right hand oriented helical thread, and the second releasing member has a left hand oriented helical thread. In a further embodiment, the first releasing member also includes a left hand oriented helical thread, while the second releasing member also includes a right hand oriented helical thread.

In one embodiment, the method includes rotating said second releasing member in a second direction while performing the step of rotating said first releasing member in a first direction. In another embodiment, the method includes rotating said second releasing member in a first direction while performing the step of rotating said first releasing member in a second direction. In one embodiment, the first direction is a clockwise direction and the second direction is a counter-clockwise direction. In another embodiment, the step of releasing the sample holder from the first releasing member while simultaneously releasing the sample holder from the second releasing member.

DESCRIPTION OF THE DRAWINGS

FIGS. 6A-C are successive perspective views of a releasing member, according to one embodiment of the invention, as it rotates in a clockwise direction.

FIGS. 7A-C are successive perspective views of a releasing member, according to one embodiment of the invention, as it rotates in a counter-clockwise direction.

DETAILED DESCRIPTION OF THE INVENTION

Automated sample analyzers are used for detecting a substance, such as a contaminant or an analyte, in a sample. For example, a sample may be an environmental sample such as a soil or water sample, or the sample may be from a human or animal patient, such as a blood or urine sample. An automated sample analyzer can analyze a sample according to a predetermined protocol that may include, for example, providing a sample holder, providing a sample, adding reagents, aspirating the sample, and detecting the contents of a sample.

The invention, as described herein, discloses a cuvette dispenser for use with an automated sample analyzer. A cuvette dispenser, according to the invention, dispenses sample holders in a manner that reduces operator intervention with the dispenser. According to the invention, after an operator loads the cuvette dispenser with sample holders, the cuvette dispenser manages the task of distributing individual sample holders to the automated sample analyzer as needed, which reduces the need for operator intervention. Furthermore, the cuvette dispense mechanism is designed to reduce malfunction, thereby improving the efficiency of the cuvette dispenser and the automated sample analyzer.

Automated Sample Analyzer

Figure 1:
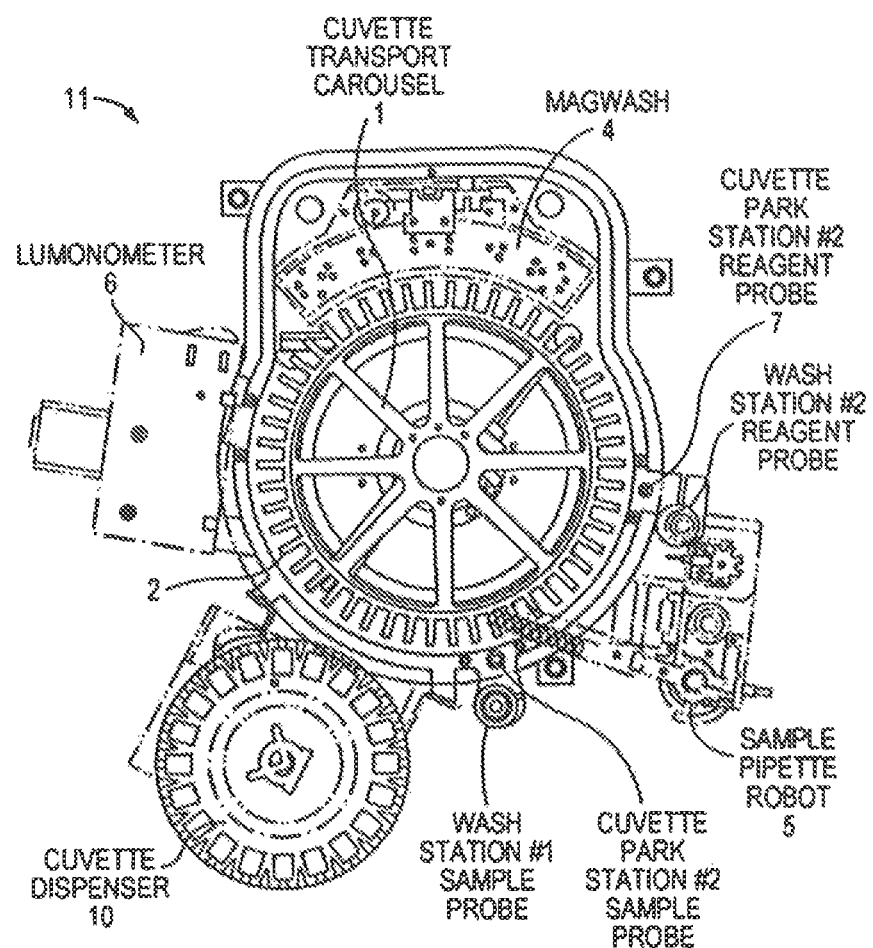
FIG. 1 is a top plan view of an automated sample analyzer having a cuvette dispensing station, according to an illustrative embodiment of the invention.

FIG. 1 is a top view of an automated sample analyzer having a cuvette loading station, according to an illustrative embodiment of the invention. According to one illustrative embodiment of the invention, the automated sample analyzer 11 has a cuvette dispensing station 10 positioned adjacent a cuvette transport carousel 1. The cuvette dispensing station 10 dispenses empty cuvettes 12 (not shown) for retrieval by a cuvette transfer arm 14 (not shown), which transfers cuvettes 12 from the cuvette dispensing station 10 to the cuvette transport carousel 1.

Figure 2:
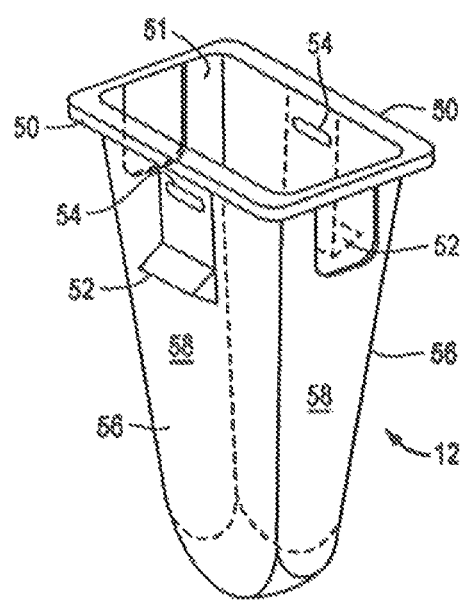
FIG. 2 is a perspective view of a cuvette for holding a sample and for dispensing from a cuvette dispensing station, according to an illustrative embodiment of the invention.

An exemplary sample cuvette 12 according to the invention is shown in FIG. 2. According to one embodiment, the cuvette 12 is a container that has two side walls 56 and two end walls 58. In a further embodiment, cuvette 12 has a lip or flange 50 extending around the opening 51 of the cuvette 12. For example, the lip 50 protrudes at approximately 90° from the side walls 56 in one embodiment, while in another embodiment, the lip 50 protrudes at approximately 90° from the end walls 58. Alternatively, the lip 50 extends around the perimeter of the opening 51.

With continued reference to FIG. 2, in a further embodiment, the cuvette 12 has a projection 52 on a side wall 56 for engaging a groove, hole or recess 54 in another cuvette 12. In yet another embodiment, the cuvette 12 has a first projection 52 on a first side wall 56 and a second projection 52 on a second side wall 56. In another embodiment, the cuvette 12 has a groove, hole or recess 54 on a side wall 56 for being engaged by a projection 52 from another cuvette 12. In yet another embodiment, the cuvette 12 has a first recess 54 on a first side wall 56 and a second recess 54 on a second side wall 56. For example, when a first cuvette 12 is inserted into a second cuvette 12, the first projection 52 of the first cuvette engages a groove 54 on a first side wall 56 of the second cuvette 12 and a second projection 52 on the first cuvette 12 engages a groove 54 on a second side will 56 of the second cuvette 12 to releasably secure the first cuvette 12 to the second cuvette 12 to form a stack of cuvettes 120.

As used herein, a stack of cuvettes 120 means at least two cuvettes 12 that are releasably joined to one another. Releasably joined means that the earth's gravitational forces alone are not sufficient to separate a bottom cuvette 12 from a top cuvette 12 when the two cuvettes are joined, but that the addition of an external force to separate the bottom cuvette, the first cuvette, from the top cuvette, i.e., the second cuvette is necessary. The number of cuvettes in a stack may be 2-500, preferably 10, 20, 25, 30, 50, or 100, for example.

In another embodiment, the cuvette 12 has a projection 52 on the end wall 58, while in a further embodiment, the cuvette 12 has a groove, hole or recess 54 on the end wall 58. In a different embodiment, the cuvette 12 has a first projection 52 and first recess 54 on a first end wall 58 and a second projection 52 and a second recess 54 on a second end wall 58.

Referring again to FIG. 1, the cuvette transport carousel 1 has a series of slots 2 for receiving a cuvette 12. According to one embodiment of the invention, the cuvette transport carousel 1 rotates in both the clockwise and counter clockwise directions in order to position cuvettes 12 held in the slots 2 at different stations adjacent to the cuvette transport carousel 1 in the automated sample analyzer. For example, in one embodiment, cuvette transport carousel 1 rotates to position a cuvette 12 near the sample pipette robot 5 so that the sample pipette robot 5 can dispense a sample from a sample carousel (not shown) into the cuvette 12.

In another embodiment, the cuvette transport carousel 1 rotates to position a cuvette 12 at a reagent dispensing station 7. At the reagent dispensing station, according to one embodiment of the invention, one or more reagents (not shown), such as buffers or magnetic particles having antigens or antibodies bound thereto, for example, are dispensed into the sample cuvettes 12 by one or more reagent pipettes (not shown).

In a further embodiment, the cuvette transport carousel 1 rotates to position a cuvette 12 at a magnetic particle washing station 4. Cuvettes 12 are removed from the cuvette transport carousel 1 wherein the magnetic beads added to the cuvette 12 at the reagent dispense station 7 are washed according to methods described in the concurrently filed U.S. patent application entitled "Magnetic Particle Washing Station"Ser. No. 11/704,138.

In yet another embodiment, the cuvette transport carousel 1 rotates to position the cuvette 12 near an analysis station 6. For example, in one embodiment according to the invention, the analysis station is a luminometer 6. The cuvettes 12 are removed from the cuvette transport carousel 1 and positioned inside the luminometer 6 one at a time. In one embodiment, the luminometer 6 provides a sealed environment free from outside light for performing chemiluminescent assays which measure, for example, target molecules in the sample.

Cuvette Dispenser

Figure 3A:
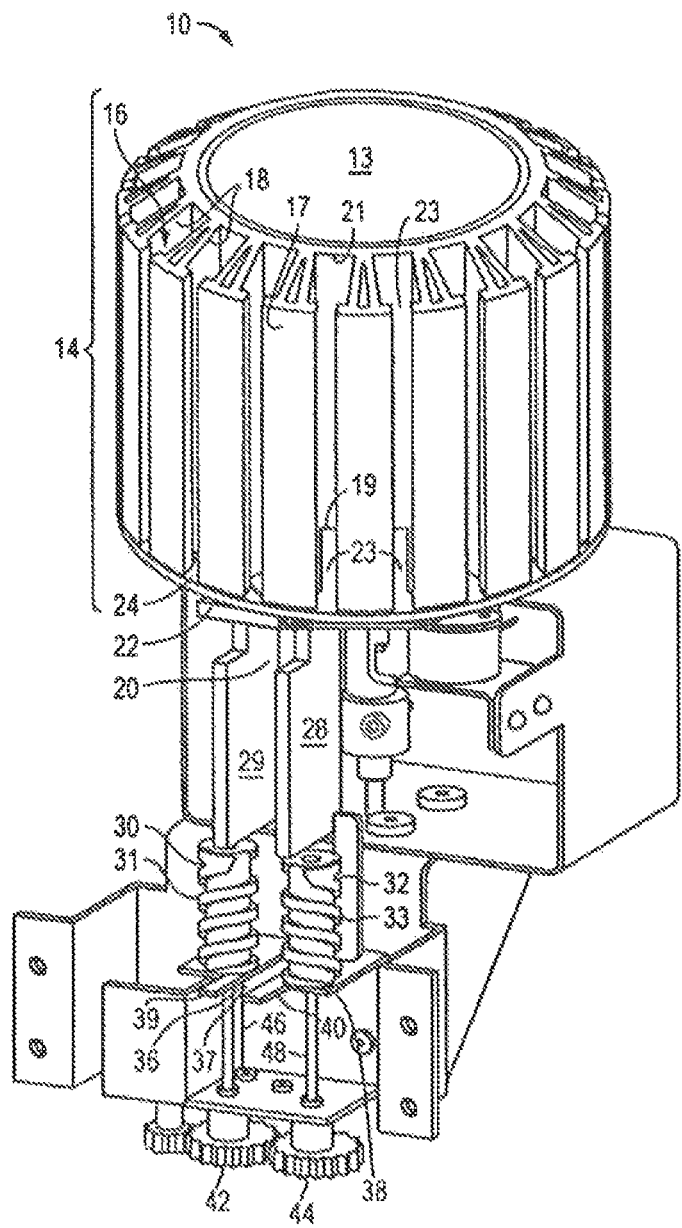
FIG. 3A is a plan view of a cuvette dispenser of an automated sample analyzer including a cuvette loading module on the top portion to receive stacks of cuvettes, according to an illustrative embodiment of the invention.
Figure 3B:
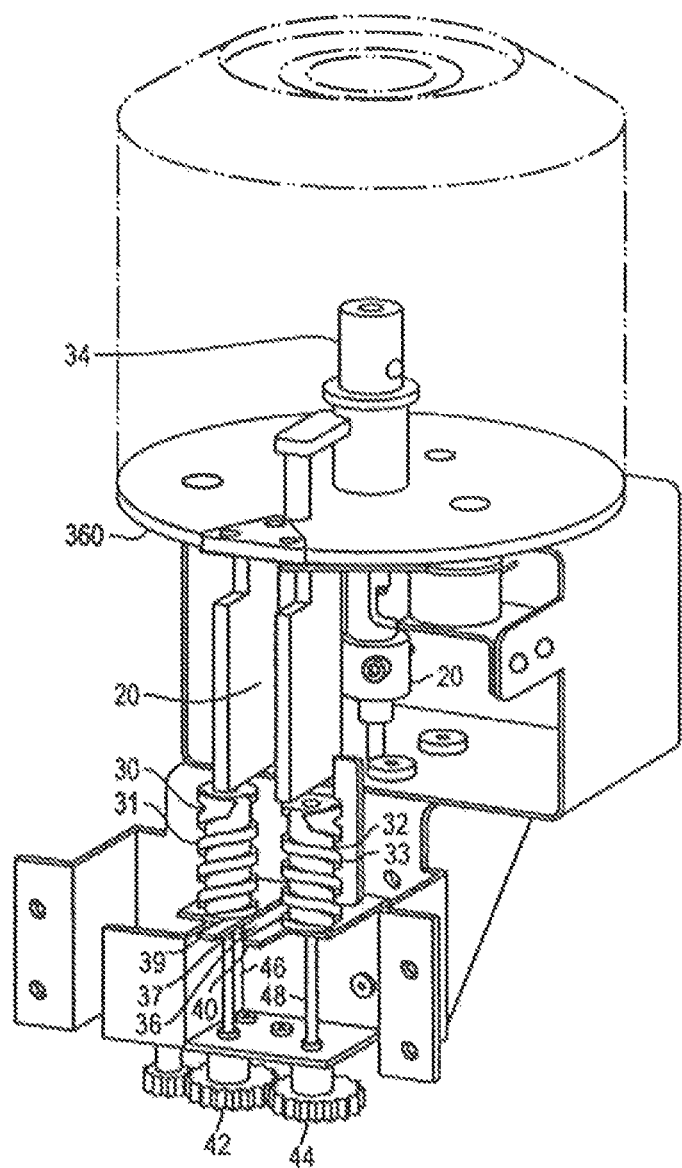
FIG. 3B is a perspective view of the cuvette dispenser of an automated sample analyzer as shown in FIG. 3A, with the cuvette loading module removed to reveal an engagement piece for engaging and rotating the cuvette loading module, according to one illustrative embodiment of the invention.

FIG. 3A is a perspective view of a cuvette dispenser of an automated sample analyzer, including a cuvette loading module for receiving stacks of cuvettes, according to an illustrative embodiment of the invention, while FIG. 3B is a perspective view of the cuvette dispenser of an automated sample analyzer as shown in FIG. 3A, but with the cuvette loading module removed to reveal an engagement piece for engaging and rotating the cuvette loading module according to one illustrative embodiment of the invention.

As shown in FIGS. 3A-B, according to one embodiment, the cuvette dispenser 10 includes a cuvette loading module 14, a cuvette dispense chute 20, one or more cuvette release members 30, 32, and a cuvette transfer position 36. The cuvette loading module 14 has a plurality of slots 16 for holding stacks of cuvettes 120. The cuvette dispense chute 20 receives stacks of cuvettes 120 from the cuvette loading module 14 and provides them to the one or more cuvette release members 30, 32. Cuvette release members 30, 32 separate individual cuvettes 12 from the stack of cuvettes 120, depositing individual cuvettes 12 one at a time to the cuvette transfer position 36.

According to one embodiment of the invention, the cuvette loading module is positioned above the cuvette dispense chute 20 and the cuvette release members 30, 32. In one embodiment, the cuvette loading module 14 is circular, for example, a wheel, disc, or cylinder. In a further embodiment, the cuvette loading module 14 has a plurality of vertically oriented slots 16 extending from the top 13 of the module 14 to the bottom 24 of the module 14 for receiving stacks of cuvettes 120. The module 14 has, for example, 15, 20, or 25 slots 16. Each slot 16 includes two side walls 18. The side walls 13 of the slot 16 abut a rear wall 21. According to one embodiment of the invention, each slot 16 is spaced an equal distance from the center of the circular module 14. In a further embodiment, each slot 16 is equally distributed around the perimeter of the module 14.

In a further embodiment of the cuvette loading module 14, each side wall 18 has a lip 17 for securing the stack of cuvettes 120. In another embodiment, between lip 17 of the first side wall and lip 17 of the second side wall 18, there is a gap 23. The gap 23 allows an operator to see whether or not a slot 16 is empty or filled with cuvettes 12, thus improving ease of operation. In a further embodiment, rear wall 21 includes a window 19 for allowing a sensor (not shown) to detect the presence or absence of a cuvette 12.

According to one embodiment, the cuvette loading module 14 rotates about a central axis. The module 14 sits on a base plate 360 and engages a central pin 34. The pin 34 is operatively connected to a motor (not shown), for example, by an axle or shaft. The pin 34 rotates causing the module 14 to rotate to position a stack of cuvettes 120 above a cuvette shutter 22. In one embodiment, while the module 14 rotates, the base plate 360 remains stationary. In a further embodiment, the base plate 360 supports the base of the cuvette stack 120.

Figure 4:
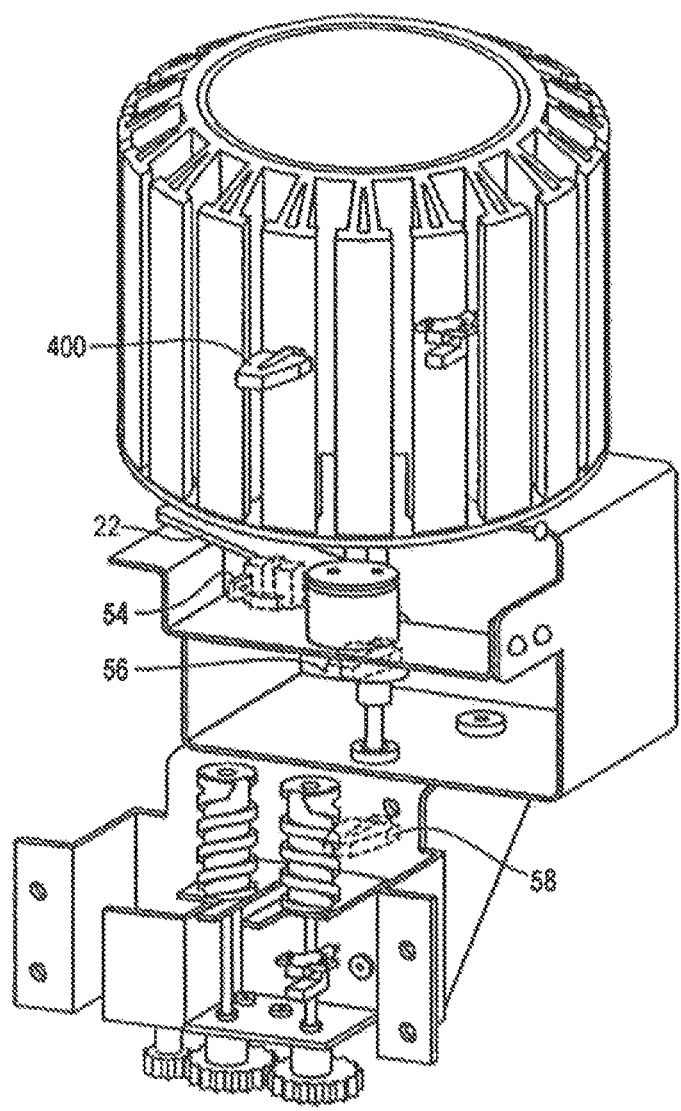
FIG. 4 is a perspective view of a cuvette dispenser of an automated sample analyzer including several sensors for activating movement of cuvettes through the cuvette dispenser, according to one illustrative embodiment of the invention.

FIG. 4 is a perspective view of a cuvette dispenser of an automated sample analyzer showing several sensors for activating movement of cuvettes through the cuvette dispenser, according to one illustrative embodiment of the invention. In one embodiment, a cuvette stack sensor 400 is fixed to the base plate 360. According to another embodiment of the invention, the cuvette stack sensor 400 detects the presence or absence of a stack of cuvettes 120 in the slots 16. For example, in one embodiment, the cuvette stack sensor 400 detects the presence or absence of a cuvette stack 120 via the window 19 in the rear wall 21 of the slot 16. For example, if a cuvette is not detected in the slot 16, the sensor 400 detects the absence of the cuvette stack 120 and the cuvette loading module 14 rotates to position a stack of cuvettes 120 over the cuvette shutter 22.

Figure 5A:
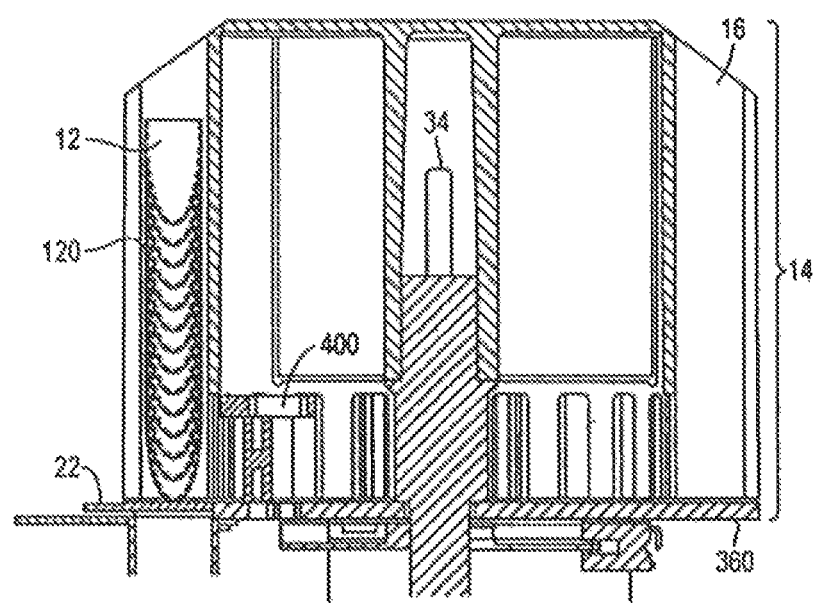
FIG. 5A is a cross-sectional view of a cuvette loading module housing a stack of cuvettes prior to the cuvettes being released into the cuvette dispense chute for distribution, according to one illustrative embodiment of the invention.

FIG. 5A is a cross-sectional view of a cuvette loading module housing a stack of cuvettes prior to the cuvettes being released into the cuvette dispense chute for distribution, according to one illustrative embodiment of the invention. Once the cuvette stack 120 is positioned over the cuvette shutter 22, as shown in FIG. 5A, the cuvette stack sensor 400 detects a cuvette, activating the cuvette shutter 22 to open. In one embodiment, the cuvette shutter 22 pivots in the plane of the base plate 360 to open and close over a cuvette chute 20, described below in greater detail. In another embodiment, the cuvette shutter 22 pivots in a plane not parallel to the base plate 360. For example, the cuvette shutter 22, in one embodiment, is a door that opens from a plane parallel to the base plate 360 to a plane that is substantially perpendicular to the base plate 360.

Figure 5B:
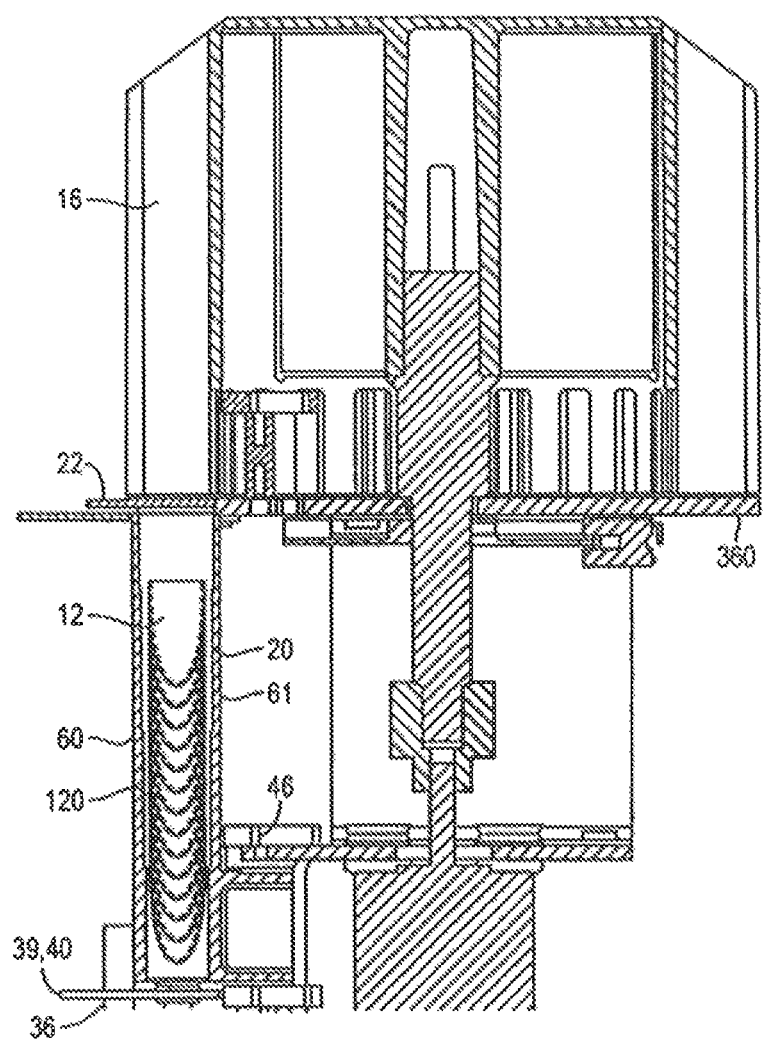
FIG. 5B is a cross-sectional view of a cuvette dispenser including the cross-sectional view of the cuvette loading module of FIG. 5A, wherein the stack of cuvettes shown in FIG. 5A has been released into the cuvette dispense chute, according to one illustrative embodiment of the invention.

FIG. 5B is a cross-sectional view of the cuvette dispenser. The stack of cuvettes shown in FIG. 5A has been released into a cuvette dispense chute, according to one illustrative embodiment of the invention. Once the cuvette shutter 22 opens, the cuvette stack 120 drops from the cuvette loading module 14 into cuvette dispense chute 20, for example. At this point, the cuvette 12 at the bottom of the stack rests on a first cuvette release member 30 and a second cuvette release member 32, while the remaining cuvettes are supported by the chute 20.

According to one embodiment of the invention, the chute 20 is a tube, for example, a rectangular tube, a square tube or a cylindrical tube, sized and shaped to receive a plurality of cuvettes 12, e.g., a stack of cuvettes 120. In a further embodiment, the tube 20 is open on the front portion 60, while in another embodiment, the tube is closed over the front portion 60. In another embodiment, the chute 20 includes a first parallel wall 28 and a second parallel wall 29 to support cuvettes 12, thereby permitting visibility of the cuvettes 12 in the chute. For example, in one embodiment, the cuvette dispense chute 20 is a pair of parallel walls, each shaped in cross-section like a square bracket ([ ]) providing a hollow passage between the walls to support a stack of cuvettes 120.

Referring again to FIG. 4, once the stack of cuvettes 120 is present in the cuvette dispense chute 20, a cuvette dispense sensor 56, positioned for example, at the base of the cuvette dispense chute 20, detects the presence of the cuvette stack 120, according to one embodiment of the invention. Upon detecting the presence of a cuvette stack 120, the first cuvette release member 30 and second cuvette release member 32 rotate to release a cuvette 12 from the cuvette stack 120. The cuvette dispense chute 20 supports the cuvettes 12 until they are removed from the stack 120 by the first cuvette release member 30 and second cuvette release member 32.

FIGS. 6A-C and FIGS. 7A-C are perspective views of a first cuvette release member and a second cuvette release member respectively. As shown in FIGS. 6A-C and FIGS. 7A-C, the first cuvette release member 30 and the second cuvette release member 32 are cylindrical in shape. In one embodiment, the first cuvette release member 30 has the same diameter as the second cuvette release member 32. In another embodiment, the first cuvette release member 30 has a diameter that is different from the diameter of the second cuvette release member 32 (not shown). In an alternate embodiment, however, the first cuvette release member 30 and the second cuvette release member 32 are tapered (not shown). For example, in one embodiment, the widest part of the tapered first cuvette release member 30 is the bottom of the cuvette release member 30, while in another embodiment, the widest part of the tapered cuvette release member 30 is the top of the cuvette release member 30.

With continued reference to FIGS. 6A-C and FIGS. 7A-C, according to one embodiment of the invention, the cuvette release members 30, 32 are threaded, for example, like the windings on a screw. According to one embodiment, the first cuvette release member 30 has a helical thread 31 that is in a first orientation while the second cuvette release member 32 has a helical thread in a second orientation 33. For example, in one embodiment, the first cuvette release member 30 has a right hand oriented helical thread 31 disposed on the cuvette release member 30, while the second cuvette release member 32 has a left hand oriented helical thread 33 disposed on the cuvette release member 32. In a further embodiment, the first cuvette release member 30 has a right hand oriented thread 1135 as well as a left hand oriented helical thread 1131 disposed on the cuvette release member 30. In a further embodiment, the second cuvette release member 32 has a left hand oriented helical thread 1136 as well as a right hand oriented helical thread 1132 disposed on the cuvette release member 32.

In an alternate embodiment, the first cuvette release member 30 has a helical thread 31 that is in the same orientation as the helical thread 33 of the second cuvette release member 32. For example, the first cuvette release member 30 and the second cuvette release member 32 each have a helical thread 31, 33 with a right hand orientation, while in another embodiment, the first cuvette release member 30 and the second cuvette release member 32 each have a helical thread 31, 33 with a left hand orientation. In one embodiment, a cuvette release member 30, 32 has only one thread, while in another embodiment, a cuvette release member 30, 32 has two or more threads.

With continued reference to FIGS. 6A-C and FIGS. 7A-C, in a further embodiment, the first cuvette release member 30 has a thread 1131 of a first orientation at the top end 131. The orientation of the thread 1131 reverses direction on the cuvette release member 30 to become a thread of a second orientation 1135. The thread 1131 reverses direction at a reversal point 1133 which is about 5-45% along the length of the axis of the cuvette release member 30, the axis running from the top end 131 of the cuvette release member 30 to the bottom end 231 of the cuvette release member. Preferably the thread 1131 reverses direction at a reversal point 1133 which is about 10-35%, about 15-30%, or more preferably at a point about 25% along the length of the axis of the cuvette release member 30. For example, in one embodiment, the first cuvette release member 30 has a left hand oriented thread 1131 originating from or near the top portion 131 of the first cuvette release member 30. In one embodiment, after making approximately a full turn (360 degrees) around the cuvette release member 30, the left hand orientation 1131 of the thread is reversed to a right hand orientation 1135 at a point 1133.

In a further embodiment, the second cuvette release member 32 has a thread 1132 of a first orientation at the top end 132. The orientation of the thread 1132 reverses direction on the cuvette release member 32 to become a thread of a second orientation 1136. The thread reverses direction at a reversal point 1134 which is about 5-45% along the length of the axis of the cuvette release member 32, the axis running from the top end 132 of the cuvette release member 32 to the bottom end 232 of the cuvette release member. Preferably the thread 1132 reverses direction at a reversal point 1134 which is about 10-35%, about 15-30%, or more preferably at a point about 25% along the length of the axis of the cuvette release member 32. For example, in one embodiment, the first cuvette release member 32 has a right hand oriented thread 1132 originating from or near the top portion 132 of the first cuvette release member 32. In one embodiment, after making approximately a full turn (360 degrees) around the cuvette release member 32, the right hand orientation of the thread 1132 is reversed to a left hand orientation 1136 at a reversal point 1134.

With continued reference to FIGS. 6A-C and FIGS. 7A-C, in a further embodiment, the pitch of the helical thread 31 of the first cuvette release member 30 is the same as the pitch of the helical thread 33 of the second cuvette release member 32. In a further embodiment, the pitch of the helical threads 31, 33 on the first and second cuvette release members 30, 32 is between about 6° and 10°, and in a further embodiment, the pitch is about 7°.

With reference to FIGS. 6A-C, in a further embodiment, the first cuvette release member 30 has a first portion of a helical thread in a first orientation 1131 having a first pitch and a second portion of the helical thread in a second orientation 1135 having a second pitch. The first portion of the helical thread 1131, after making approximately a full turn (360 degrees) around the cuvette release member 30, reverses orientation at a reversal point 1133 and a second portion of the helical thread 1135 having a second pitch continues turning around the cuvette release member from the reversal point 1131. For example, the second portion 1135 makes one, two, three, or four full turns around the cuvette release member 30. In one embodiment, the first pitch is between about 9.2° and 9.6° and the second pitch is between about 6.9° and 7.3°. In a further embodiment, the first pitch is about 9.4° and the second pitch is about 7.1°.

With reference to FIGS. 7A-C, in another embodiment, the second cuvette release member 32 has a first portion of a helical thread in a first orientation 1132 having a first pitch and a second portion of the helical thread in a second orientation 1136 having a second pitch. The first portion of the helical thread 1132, after making approximately a full turn (360 degrees) around the cuvette release member 30, reverses orientation at a reversal point 1134 and a second portion of the helical thread 1136 having a second pitch continues turning around the cuvette release member from the reversal point 1134. For example, the second portion 1136 makes one, two, three, or four turns around the cuvette release member 30. In one embodiment, the first pitch is between about 9.2° and 9.6° and the second pitch is between about 6.9° and 7.3°. In a further embodiment, the first pitch is about 9.4° and the second pitch is about 7.1°.

As used herein, the pitch of a helical thread 31, 33 means the angle formed between the helical thread and a plane that intersects the helical thread 31, 33, the plane being perpendicular to the longitudinal axis of the cuvette release member 30, 32.

As shown in FIGS. 3A-3B, the first cuvette release member 30 and the second cuvette release member 32 rotate in an axis parallel to the axis of the cuvette stack 120, according to one embodiment of the invention. In another embodiment, first cuvette release member 30 and the second cuvette release member 32 rotate around an axis perpendicular to the cuvette stack 120.

Referring again to FIGS. 3A-B, cuvette release members 30, 32 are each connected to a rotating member 42. For example, in one embodiment, an exemplary rotating member is a gear wheel 42 as shown in FIGS. 3A-B. The gear wheel 42 is operatively connected to a motor (not shown), for example, an oscillating motor, capable of effecting the rotation of the gear wheels 42, and thereby the rotation of the cuvette release member 30. For example, in one embodiment, the first cuvette release member 30 is connected to a first rotating member 42 by axle 46 and the second cuvette release member 32 is connected to a second rotating member 44 by axle 48.

The first rotating member 42 and the second rotating member 44, in one embodiment, are each capable of rotating in both the clockwise or counter-clockwise direction to effect the rotation of the first cuvette release member 30 and the second cuvette release member 32, respectively. For example, in one embodiment, the first cuvette release member 30 and the second cuvette release member 32 each rotate in the same direction, for example, clockwise, or alternatively, counter-clockwise.

In yet another embodiment, the first cuvette release member 30 rotates in a direction opposite from the second cuvette release member 32. For example, the first cuvette release member 30 rotates in a clockwise direction while the second cuvette release member 32 rotates in a counter-clockwise direction. Alternately, in another embodiment, the first cuvette release member 30 rotates in a counter-clockwise direction while the second cuvette release member 32 rotates in a clockwise direction.

In an even further embodiment, the first cuvette release member 30 rotates in a first direction, e.g., clockwise, for a first period of time, while the second cuvette release member 32 rotates in a second direction, e.g., counter-clockwise, for a first period of time, after which the first cuvette release member 30 reverses to rotate in a second direction for a second period of time and the second cuvette release member 32 simultaneously reverses to rotate in a first direction for a second period of time.

Figure 8A:
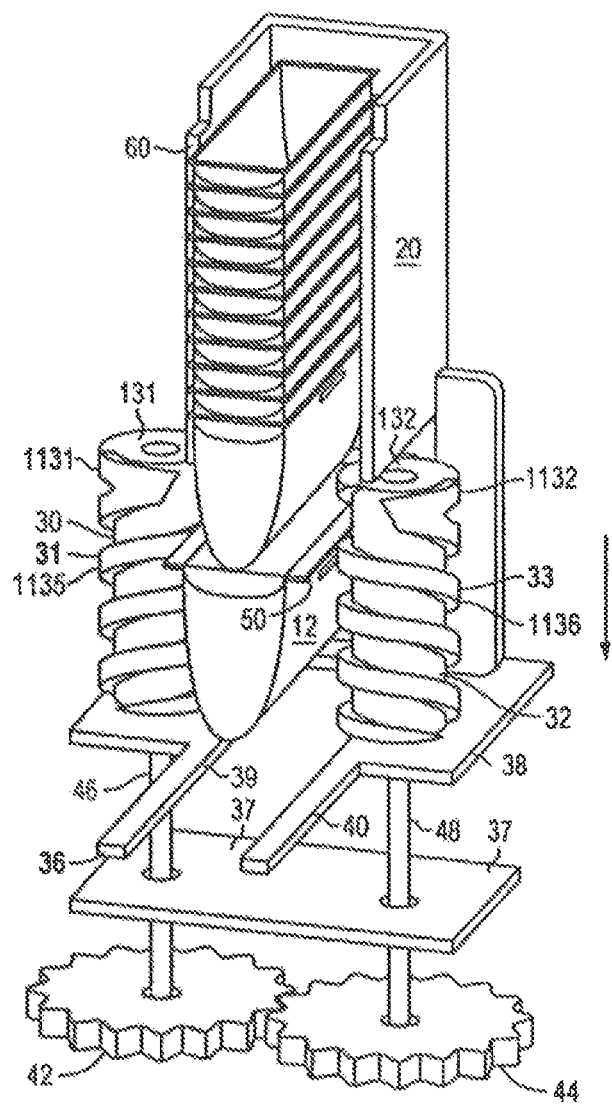
FIGS. 8A-C are perspective views of cuvette release members for releasing a cuvette from a stack of cuvettes in the cuvette dispense chute, wherein the cuvette release members are threaded and rotate to engage the cuvette to remove it from the stack and dispense it at the cuvette transfer position according to an illustrative embodiment of the invention.
Figure 8B:
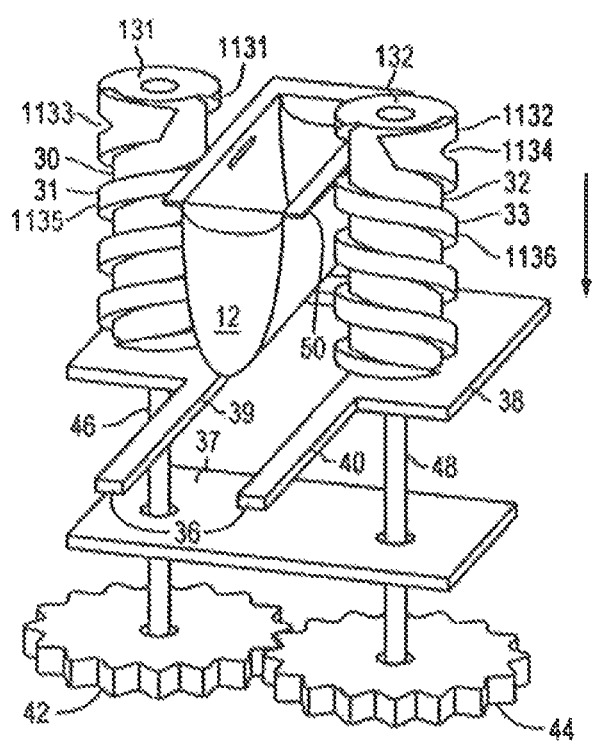
Figure 8C:
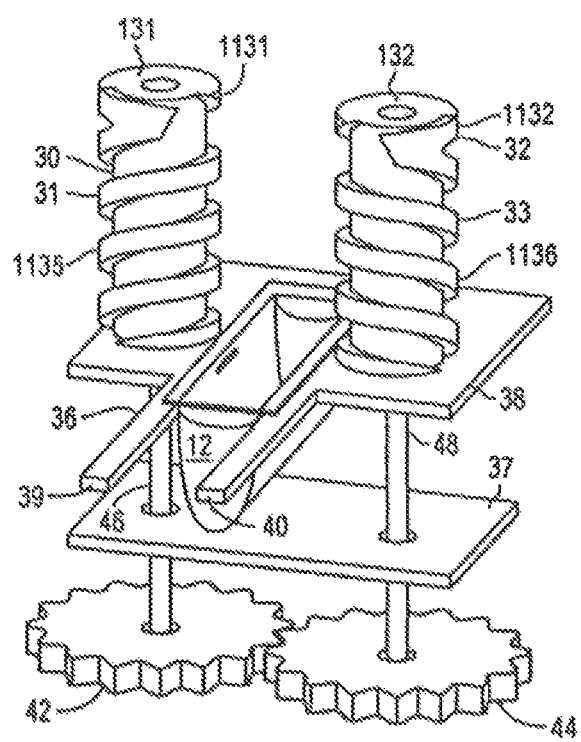

FIGS. 8A-C are perspective views of cuvette release members for releasing a cuvette from a stack of cuvettes in the cuvette dispense chute. The exemplary first cuvette release member 30 and second cuvette release member 32 are threaded and rotate to engage, the cuvette 12 to remove it from the stack 120. Once the cuvette 12 has traveled fully through the cuvette release member 30, 32, the cuvette 12 is dispensed at the cuvette transfer position 36 according to an illustrative embodiment of the invention. As discussed above, once the cuvette shutter 22 opens, a stack of cuvettes 12 moves downward until the bottom cuvette 12 in the cuvette stack 120 comes to rest on the first cuvette release member 30 and the second cuvette release member 32, according to one embodiment of the invention. The cuvette dispense sensor 58 detects the presence of the cuvettes 12, the bottom cuvette 12, and the first cuvette release member 30 and the second cuvette release member 32 begin to rotate to release the cuvette from the stack 120.

As shown in FIG. 8A, according to one embodiment of the method of the invention, the first cuvette release member 30 and the second cuvette release member 32, described above with respect to FIGS. 6A-C and FIGS. 7A-C, rotate to engage the lip 50 of the cuvette 12 to effect the cuvette's 12 separation from the stack of cuvettes 120. Alternately, in one embodiment, the first cuvette release member 30 rotates while the second cuvette release member 32 is stationary; when the first cuvette release member 30 stops rotating, the second cuvette release member 32 rotates. In yet another embodiment, the first cuvette release member 30 rotates simultaneously with the second cuvette release member 32.

In a further embodiment, the first cuvette release member 30 rotates in a first direction, e.g., clockwise, while the second cuvette release member rotates in a second direction, e.g., counter-clockwise, in order to engage the lip 50 of the cuvette 12 and to separate it from the stack 120. In yet another embodiment, the first cuvette release member 30 rotates in a first direction, e.g., clockwise, both to engage the lip 50 of the cuvette 12 and to release the cuvette 12 into the cuvette transfer position 36, while the second cuvette release member 32 rotates in a second direction, e.g., counter-clockwise, both to engage the lip 50 of the cuvette 12 and to release the cuvette 12 into the cuvette transfer position 36. In a further embodiment, the first cuvette release member 30 rotates in a first direction e.g., clockwise, while the second cuvette release member rotates in a second direction, e.g., counter-clockwise, in order to engage the lip 50 of the cuvette 12 and to separate it from the stack 120; the first cuvette release member 30 and the second cuvette release member 32 then each reverse their direction of rotation in order to release the cuvette 12 into the cuvette transfer position 36.

With continued reference to FIG. 8A, according to one embodiment of the invention, the first cuvette release member 30 has a helical thread 31 having a first portion of a first orientation (e.g., left-handed) 1131 beginning at the top portion 131 of the first cuvette release member 30. The second cuvette release member 32 also has a helical thread 33 having a first portion of a second orientation (e.g., right handed) 1132 beginning at the top portion 132 of the second cuvette release member 32. The first cuvette release member 30 rotates in a first direction (e.g., clockwise) and the left cuvette release member 32 rotates in a second direction (e.g., counter-clockwise) to engage the cuvette 12 and to release it from the stack 120.

According to one embodiment, once the cuvette 12 is released from the stack 120, the rotation of the first cuvette release member 30 and the second cuvette release member 32 is reversed. In one embodiment, the rotation of the first cuvette release member 30 and the second cuvette release member 32 is reversed when the cuvette 12 engages a reversal point 1133 between the first-orientation (e.g., left handed) helical thread portion 1131 and the second-orientation thread (e.g., right handed) portion 1135 on the first cuvette release member 30, and the reversal point 1134 between the second-orientation (e.g., right handed) thread portion 1132 and the first orientation (e.g., left handed) thread portion 1136 on the second cuvette release member 32. At that point, for example, the first cuvette release member 30 changes direction to rotate in a second direction (e.g., counter-clockwise) and the second cuvette release member 32 changes direction to rotate in a first direction (e.g., clockwise). The change in rotation prevents a second cuvette 12 from being dispensed prior to the first cuvette 12 being delivered to the cuvette transfer position 36.

As shown in FIG. 8B, the helical threads 31 of the first cuvette release member 30 and the helical threads 33 of the second cuvette release member 32 continue to engage the lip 50 of the cuvette 12 after the cuvette 12 releases from the stack of cuvettes 120 and while the cuvette 12 moves in a downward direction via the cuvette release members 30, 32 toward the cuvette transfer position 36, in one embodiment, the first cuvette release member 30 and the second cuvette release member 32 engage the lips 50 of the side walls 56 of the cuvette 12, while in another embodiment, the first cuvette release member 30 and the second cuvette release member 32 engage the lips 50 of the end walls 58 of the cuvette 12.

With continued reference to FIG. 8A, according to a further embodiment, the force exerted on the cuvette 12 by the helical threads 31 of the first cuvette release member 30 and the helical threads 33 of the second cuvette release member 32 causes the projections 52 on cuvette 12 to disengage from the stack of cuvettes 120. For example, in one embodiment, the downward force exerted by the rotating first orientation (e.g., left hand) helical thread portion 1131 of the first cuvette release member 30 and the second orientation (e.g., right hand) helical thread portion 1132 of the second cuvette release member 32 causes the recesses 54 on the walls of the cuvette 12 to disengage from the projections 52 on the adjacent cuvette 12 in the stack 120.

With reference to both FIGS. 8A and 8B, as the first rotating member 30 and the second rotating member 32 continue to rotate, the cuvette 12 moves along the helical thread 31 of the first rotating member 30 and the helical thread 33 of the second rotating member 32 in a downward direction, as indicated by the directional arrow in FIG. 8A. For example, in one embodiment, once the cuvette 12 is released from the stack 120, the first cuvette release member 30 and the second cuvette release member 32 reverse rotational direction to further facilitate the cuvette traveling in a downward direction.

With continued reference to FIGS. 8A and 8B, in one embodiment, the first cuvette release member 30 has a helical thread 31 having a top portion 1131 and a bottom portion 1135. The top portion 1131 has a first orientation (e.g., left hand) and the bottom portion 1135 has a second orientation (e.g., right hand). The first orientation reverses to the second orientation at reversal point 1133. The second cuvette release member 32 also has a helical thread 33 having a top portion 1132 and a bottom portion 1136. The top portion 1132 has a first orientation (e.g., right hand) and the bottom portion 1136 has a second orientation (e.g., left hand). The first orientation reverses to the second orientation at reversal point 1134. When the rotational direction of the first cuvette release member 30 and the second cuvette release member 32 reverses, the cuvette 12, in one embodiment, then travels along the bottom portion 1135 of the first cuvette release member 30 helical thread 31 and the bottom portion 1136 of the second cuvette release member 32 helical thread 33 in a downward direction toward the cuvette transfer position 36.

Figure 5C:
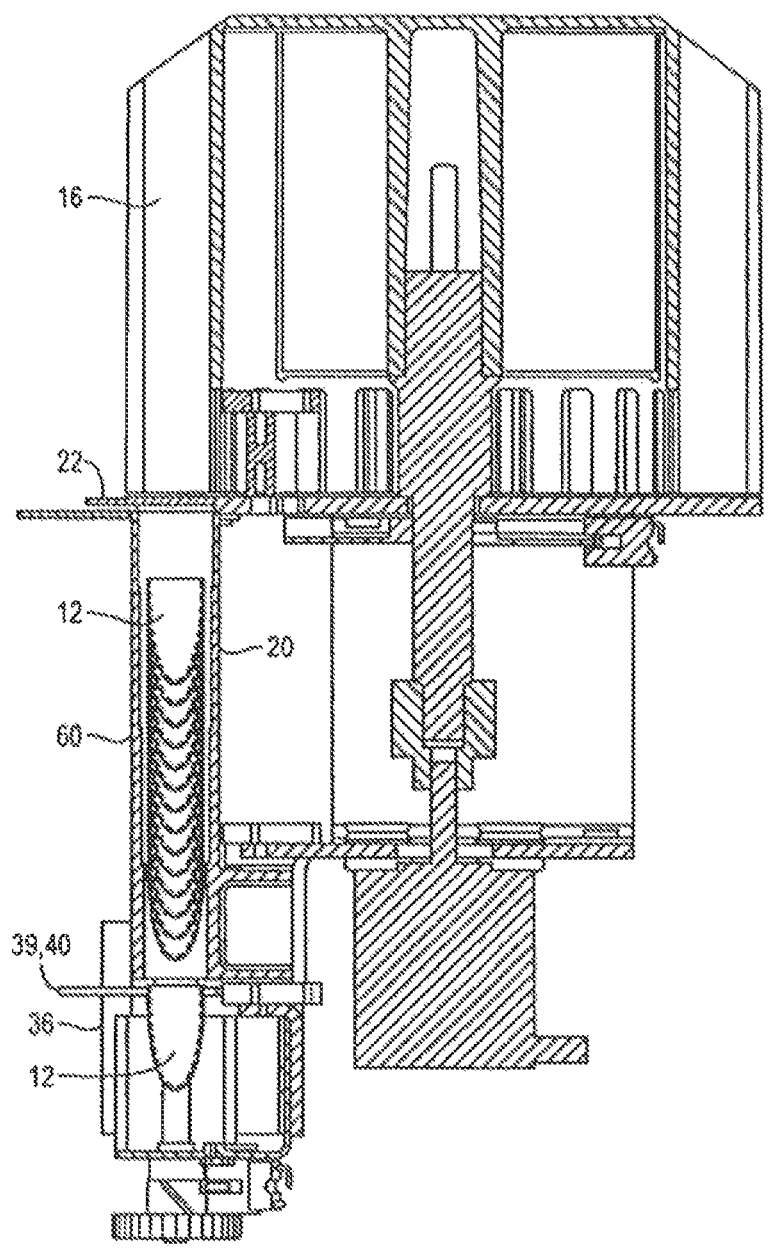
FIG. 5C is a cross-sectional view of the cuvette dispenser shown in FIG. 5B, wherein a cuvette from the stack of cuvettes has been released from the cuvette release members to the cuvette transfer position, according to one illustrative embodiment of the invention.

FIG. 5C is a cross-sectional view of the cuvette dispenser shown in FIG. 5B, while FIG. 8C shows a perspective view of the cuvette dispenser. A cuvette from the stack of cuvettes has been released from the exemplary cuvette release members to the cuvette transfer position, according to one illustrative embodiment of the invention. According to one embodiment of the invention, the cuvette transfer position 36 is located directly below and between the first cuvette release member 30 and the second cuvette release member 32. As shown in FIG. 3A, the cuvette release members 30, 32 rest on a platform 38. In one embodiment, the cuvette transfer position 36 includes a first projection 39 and a second projection 40 from the platform 38. A space 37 separates the first projection 39 from the second projection 40. For example, the space 37 receives the body of the cuvette 12, while the lips 50 of the cuvette 12 rest on the first projection 39 and the second projection 40 according to one embodiment of the invention.

Referring again to FIG. 4, once the cuvette 12 is positioned in the cuvette transfer position 36, a cuvette transfer sensor 48 detects the presence of the cuvette 12, and stops the first cuvette release member 30 and the second cuvette release member 32 from rotating. This prevents another cuvette 12 from occupying the cuvette transfer position 36, until the cuvette 12 currently occupying the cuvette transfer position 36 is removed. In a further embodiment, once a cuvette 12 is present at the cuvette transfer position 36, the cuvette transfer sensor 48 signals to a robotic arm (not shown), for example, to remove the cuvette 12 from the transfer position 36 and to place it on the cuvette transport carousel 1.

According to one embodiment of the invention, once the cuvette 12 is removed from the cuvette transfer position 36, the cuvette transfer sensor 48 detects the absence of a cuvette 12, signaling the first cuvette release member 30 and the second cuvette release member 32 to rotate and provide another cuvette 12 to the cuvette transfer position 36. Once the stack of cuvettes 120 in the cuvette dispense chute 20 has been dispensed, the cuvette dispense sensor 56 detects the absence of cuvettes 12, causing the cuvette loading module 14 to rotate until the cuvette stack sensor 400 detects a stack of cuvettes 120, at which point the process of dispensing cuvettes 12 proceeds as previously discussed.

In another aspect, the invention is a method for automatically loading a plurality of cuvettes 12 onto a conveyor, such as a rotating cuvette carousel 1, in an automated clinical sample analyzer. For example, in one embodiment, an operator first loads stacks of cuvettes 120 into the slots 16 of the cuvette loading module 14. The module 14 rotates until the cuvette stack sensor 400 detects the presence of a stack of cuvettes 120 over the cuvette shutter 22.

Once a stack of cuvettes 120 is positioned over the cuvette shutter 22, the cuvette shutter 22 opens and the stack of cuvettes 120 falls into the cuvette chute 20, with the bottom cuvette 12 of the stack 120 resting on the first cuvette releasing member 30 and the second cuvette releasing member 32. Cuvette dispense sensor 56 detects the presence of the cuvette stack 120 and causes the first cuvette release member 30 and the second cuvette release member 32 to rotate to engage and release a cuvette 12 from the stack 120, and to deliver the cuvette to the cuvette transfer position 36.

In one embodiment, the first cuvette release member 30 rotates in a first direction, e.g., clockwise, while the second cuvette release member 32 rotates in a second direction, e.g., counter-clockwise to engage the cuvette 12; the first cuvette release member 30 then switches direction to rotate in a second direction while the second cuvette release member 32 switches direction to rotate in a first direction to release cuvette 12 to the cuvette transfer position 36. In another embodiment, the first cuvette release member 30 rotates in a first direction, e.g., clockwise, both to engage the cuvette 12 and to release the cuvette 12 at the cuvette transfer position 36, while the second cuvette release member 32 rotates in a second direction, e.g., counter-clockwise, both to engage the cuvette 12 and to release cuvette 12 at the cuvette transfer position 36.

Once the cuvette 12 rests in the cuvette transfer position 36, cuvette transfer sensor 58 signals to a robotic arm (not shown), for example, to remove the cuvette 12 from the transfer position 36 and to place it in a slot 2 of the cuvette transport carousel 1.

Variations, modifications, and other implementations of what is described herein will occur to those of ordinary skill in the art without departing from the spirit and the scope of the invention as claimed. Accordingly, the invention is not to be defined by the preceding illustrative description but instead by the spirit and scope of the following claims.

The invention claimed is:

1. A device for releasing a cuvette from a stack of cuvettes releasably joined to one another, said device comprising:
  a support member for receiving a said stack of said releasably joined cuvettes;
  a first releasing member comprising a taper and a second releasing member, said first releasing member comprising a first helical thread and said second releasing member comprising a second helical thread, each of said first releasing member and said second releasing member having a first end and a second end,
  said support member being positioned to introduce the stack of said releasably joined cuvettes least between said first releasing member and said second releasing member,
  wherein the widest part of the first releasing member is the first end or the second end of the first releasing member and wherein said first and second releasing members rotate and cooperate thereby releasing one of said releasably joined cuvettes from said stack of cuvettes.

2. The device of claim 1, wherein said first helical thread and said second helical thread are of opposite handedness, and
  said first releasing member and said second releasing member rotate in opposite directions.

3. The device of claim 1, wherein said second releasing member comprises a taper.

4. The device of claim 1, wherein the widest part of said second releasing member is the second end of said second releasing member.

5. The device of claim 1, wherein the first releasing member is operatively connected to a first rotator capable of rotation in a clockwise direction and the second releasing member is operatively connected to a second rotator capable of rotation in a counter-clockwise direction.

6. The device of claim 5, wherein the first rotator is further capable of rotation in a counter-clockwise direction while the second rotator is further capable of rotation in a clockwise direction.

7. The device of claim 5, wherein the rotator comprises a motor.

8. The device of claim 5 further comprising a sensor for activating movement of said cuvettes through a sample dispenser.

9. The device of claim 8, wherein said sensor is fixed to a base plate of said support member for receiving said stack of said cuvettes.

10. The device of claim 8, wherein said sensor detects the presence or absence of said stack of cuvettes in a slot.

11. The device of claim 1 wherein the first releasing member and the second releasing member rotate in an axis parallel to the axis of the support member.

12. The device of claim 1 wherein the first releasing member and the second releasing member rotate around an axis perpendicular to the support member.

13. The device of claim 1 wherein the first releasing member has a first portion of the helical thread in a first orientation having a first pitch and a second portion of the helical thread in a second orientation having a second pitch.

14. The device of claim 13 wherein the first portion of the helical thread, after making approximately a full turn around the releasing member, reverses orientation at a reversal point which is about 5-45% along an axis of the sample releasing member, and the second portion of the helical thread having the second pitch continues turning around the releasing member from the reversal point.

15. The device of claim 1 wherein the widest part of the first releasing member is the second end of the first releasing member.

16. The device of claim 14, wherein the axis runs from the top end of the sample releasing member to the bottom end of the sample releasing member.

* * * * *